United States Patent
Charlap

(10) Patent No.: US 11,404,170 B2
(45) Date of Patent: Aug. 2, 2022

(54) METHOD AND SYSTEM FOR PATIENTS DATA COLLECTION AND ANALYSIS

(71) Applicant: Steven Charlap, Boca Raton, FL (US)

(72) Inventor: Steven Charlap, Boca Raton, FL (US)

(73) Assignee: Soap, Inc., Boca Raton, FL (US)

( * ) Notice: Subject to any disclaimer, the term of this patent is extended or adjusted under 35 U.S.C. 154(b) by 653 days.

(21) Appl. No.: 15/490,780

(22) Filed: Apr. 18, 2017

(65) Prior Publication Data

US 2017/0300648 A1    Oct. 19, 2017

Related U.S. Application Data

(60) Provisional application No. 62/323,803, filed on Apr. 18, 2016.

(51) Int. Cl.
| | |
|---|---|
| *G16H 50/30* | (2018.01) |
| *G16H 10/60* | (2018.01) |
| *G16H 80/00* | (2018.01) |
| *G16B 20/00* | (2019.01) |
| *G16H 50/20* | (2018.01) |

(52) U.S. Cl.
CPC .......... *G16H 80/00* (2018.01); *G16B 20/00* (2019.02); *G16H 10/60* (2018.01); *G16H 50/20* (2018.01); *G16H 50/30* (2018.01)

(58) Field of Classification Search
None
See application file for complete search history.

(56) References Cited

U.S. PATENT DOCUMENTS

| | | | | |
|---|---|---|---|---|
| 6,285,367 | B1* | 9/2001 | Abrams | G06F 3/0482 715/841 |
| 2003/0046114 | A1* | 3/2003 | Davies | G06Q 10/10 705/3 |
| 2003/0113727 | A1* | 6/2003 | Girn | G16H 50/30 435/6.11 |
| 2006/0074689 | A1* | 4/2006 | Cosatto | G06T 13/40 704/275 |
| 2006/0085192 | A1* | 4/2006 | Davis | G10L 15/22 704/257 |
| 2006/0173717 | A1* | 8/2006 | Scheuner | G06Q 10/10 705/2 |
| 2008/0096533 | A1* | 4/2008 | Manfredi | G06N 3/006 455/412.1 |

(Continued)

OTHER PUBLICATIONS

C Wang et al., Acceptability and feasibility of a virtual conselor (VICKY) to collect family health histories, Jan. 15, 2015, Genetics in Medicine (Year: 2015).*

(Continued)

*Primary Examiner* — Christopher L Gilligan
*Assistant Examiner* — Karen A Hranek
(74) *Attorney, Agent, or Firm* — Merchant & Gould P.C.

(57) ABSTRACT

A conversational and embodied Virtual Assistant (VA) with Decision Support (DS) capabilities that can simulate and improve upon information gathering sessions between clinicians, researchers, and patients. The system incorporates a conversational and embodied VA and a DS and deploys natural interaction enabled by natural language processing, automatic speech recognition, and an animation framework capable of rendering character animation performances through generated verbal and nonverbal behaviors, all supplemented by on-screen prompts.

12 Claims, 6 Drawing Sheets

(56) References Cited

U.S. PATENT DOCUMENTS

| | | | | |
|---|---|---|---|---|
| 2009/0018863 | A1* | 1/2009 | Yoon | G06Q 40/08 |
| | | | | 705/2 |
| 2009/0216691 | A1* | 8/2009 | Borzestowski | G06F 16/3332 |
| | | | | 706/11 |
| 2012/0165618 | A1* | 6/2012 | Algoo | A61B 5/744 |
| | | | | 600/300 |
| 2012/0166365 | A1* | 6/2012 | Tur | G06N 5/022 |
| | | | | 706/11 |
| 2013/0096940 | A1* | 4/2013 | Hayes | G06Q 10/10 |
| | | | | 705/2 |
| 2014/0337048 | A1* | 11/2014 | Brown | G10L 15/08 |
| | | | | 705/2 |
| 2015/0286858 | A1* | 10/2015 | Shaburov | G06T 7/337 |
| | | | | 382/103 |

OTHER PUBLICATIONS

Cohn et al., Health Heritage, a Web-Based Tool for the Collection and Assessment of Family Health History: Initial User Experience and Analytic Validity, Apr. 29, 2010, Public Health Genomics 13:477-491 (Year: 2010).*

Giovanni et al., The Application of Computer-Based Tools in Obtaining the Genetic Family History, Jul. 2010, Current Protocols in Human Genetics 9.21.1-9.21.9 (Year: 2010).*

R Naphtal, Natural Language Processing Based Nutritional Application, Jun. 2015, Massachusetts Institute of Technology (Year: 2015).*

M Korpusik et al., Distributional Semantics for Understanding Spoken Meal Descriptions, Mar. 2016, ICASSP (Year: 2016).*

\* cited by examiner

|  |  |  |
|---|---|---|
| High severity epigenetic factor/low pathogenicity variant | High severity epigenetic factor/Moderate pathogenicity variant | High severity epigenetic factor/High pathogenicity variant |
| Moderate severity epigenetic factor/Low pathogenicity variant | Moderate severity epigenetic factor/Moderate pathogenicity variant | Moderate severity epigenetic factor/High pathogenicity variant |
| Low severity epigenetic factor/Low pathogenicity variant | Low severity epigenetic factor/Moderate pathogenicity variant | Low severity epigenetic factor/High pathogenicity variant | epigenetic factor → pathogenicity variant →

*Figure 5*

METHOD AND SYSTEM FOR PATIENTS
DATA COLLECTION AND ANALYSIS

RELATED APPLICATION

This application claims priority benefit from U.S. Provisional Patent Application, Ser. No. 62/323,803, filed on Apr. 18, 2016, the content of which is incorporated herein by reference in its entirety.

BACKGROUND

1. Field

This Application relates to patient and research subject medical data collection and analysis, more specifically, to the ongoing computerized collection of comprehensive family, medical, lifestyle, and environmental exposure history from a patient, using a conversational, rapport building, intelligent virtual agent, deploying personalized humor, motivational interviewing methods and performing ongoing analysis of the data to generate recommended genetic testing and nutritional, lifestyle, and weight control/loss counseling to improve or maintain health, as well as build a repository of correlated phenotype-genotype data to increase genetic variant classification and improve medical diagnosis, clinical decision-making and treatment. It also includes a new method of visualizing the risk of familial and hereditary disease risk. The humor refers to what we have titled, "Medi-tainment," short for Medical Entertainment. It is the combination of clinical acumen and medical and non-medical related humor by a virtual agent to build rapport and increased engagement with the health care user.

2. Related Arts

In early 2015, President Obama announced a research effort focusing on bringing precision medicine to many aspects of healthcare. The practice of precision medicine requires detailed patient data including family, medical, lifestyle and environmental exposure history (Comprehensive Health History or "CHH"). However, lack of time, insufficient reimbursement, and lack of knowledge to interpret such data, has most physicians and researchers either not collecting CHH or doing so at great expense of time and capital. Precision medicine also requires appropriate genotype data. Today, despite dozens of known actionable genetic tests, the failure to gather CHH and the lack of training in identifying the right genetic test(s) prevents most physicians from adopting genetic testing into practice. As a result, many patients are not benefiting from data that can help prevent, improve surveillance, and/or earlier treatment of life-threatening diseases. Much of medical research is dependent on collecting data from research subjects. This is a time-consuming, manual and tedious process that is affected by bias, boredom, tiredness, interpretation, personal chemistry, etc. As a result, research studies are limited by the cost of conducting such studies and the inaccurate information often collected. A more rapid advance of science is thereby thwarted. Accurate patient data that only a patient can provide, such as the food they eat, the chemicals they are exposed to, family medical history, etc. is critical to the advance of precision and genomic medicine, as well as all forms of research studies.

Genomic and precision medicine is based on the knowledge that virtually every medical condition, disease susceptibility or response to treatment is caused, regulated or influenced by genes. Genetic testing coupled with deep phenotype data may therefore add insightful and diagnostic value across the disease spectrum, ranging from single-gene disorders with a Mendelian inheritance pattern to complex multi-factorial diseases. Over 12 million Americans, or about 1 out of 22, are already estimated to have a genetic predisposition to life-threatening disease that may be identifiable and better managed through appropriate genetic testing. Nevertheless, genetic medicine has barely entered the realm of adult primary care, despite the increasing availability of predictive testing for cancer and other predisposing syndromes.

The first step in identifying risk for genetic disease is collecting and properly interpreting a patient's family, medical, lifestyle, and environmental exposure history. However, most physicians do not collect detailed histories due to limited time, insufficient reimbursement, limited training in inferring from such histories which genetic tests with known clinical utility are indicated, and little time and incentive to get trained. In addition, many physicians report little training in genetics; they are uncomfortable providing genetic counseling and are wary of interpreting genetic test results. Physicians also report little training in nutrition and motivational interviewing. They are uncomfortable providing nutritional and weight related counseling. Furthermore, physicians have not embraced tools that allow for patient self-collected data primarily due to lack of tool validation. Therefore, few primary care doctors are directly ordering genetic tests or referring patients to geneticists and genetic counselors for such testing. Also, other than for diabetics and end stage kidney disease, they are not referring patients for nutritional counseling. Even patients who use direct-to-consumer genetic testing labs often do so without clinician involvement.

The efficient gathering of accurate family and personal medical history is challenging. Decision-support software (e.g., Family Healthware, MeTree, etc.) has demonstrated that patient self-reported family and personal history can provide accurate and clinically actionable data, including identifying patients that may benefit from genetic and/or other diagnostic testing. Such data-driven recommendations have also been shown to prompt clinicians to implement testing they would have otherwise not been considered. However, despite these advantages, data gathering tools have limited use due to lack of validation and poor adoption by clinicians and patients. According to tool developers, (i.e. MeTree and Health Heritage), patients often forego or fail to complete extensive online medical forms due to a number of challenges, foremost among them, complex processes.

Although collecting and analyzing detailed family, medical, lifestyle and environmental exposure history is a very time-consuming process for clinicians and researchers, such information is invaluable in determining health risks, the need for actionable genetic testing, nutritional consultation, and care guidance. What is needed is a system that collects such comprehensive data in a simple, user-engaging, cost-effective, yet efficient manner, analyzes the data, and provides actionable output.

SUMMARY

The following summary of the disclosure is included in order to provide a basic understanding of some aspects and features of the invention. This summary is not an extensive overview of the invention and as such it is not intended to particularly identify key or critical elements of the invention or to delineate the scope of the invention. Its sole purpose is to present some concepts of the invention in a simplified form as a prelude to the more detailed description that is presented below.

Embodiments of the invention provide solutions that deploy a conversational Virtual Assistant (VA) with Decision Support (DS) capabilities that can simulate and improve upon by the inclusion of Medi-tainment, short for Medical Entertainment, the blending of clinical acumen, humor, and gameplay for effective and accurate information gathering sessions between clinicians, researchers and their patients and research subjects, respectively. According to disclosed embodiments, a system incorporating a VA and a DS deploys natural interaction enabled by state-of-the-art natural automatic speech recognition, natural language understanding, and an animation framework embedded in a web framework capable of rendering character animation performances through generated verbal and nonverbal behaviors, all supplemented by on-screen prompts.

Aspects of the disclosed invention include leveraging significant advances in an existing conversational agent platform with a finalized support agent with the goal of efficient and cost-effective patient data collection, using humor, empathy and motivational strategies not available in static web questionnaires. This includes an integrated, multimodal, and natural system for collecting medical, personal, and family history and an emotion model that is able to recognize emotion from the user, synthesize and express an appropriate emotional response, and build rapport with the user. The method includes the virtual agent incorporating Medi-tainment and motivational interviewing techniques in a goal-oriented, client-centered counseling style for eliciting behavior change and action by helping users to explore and resolve ambivalence.

The collected information will then be processed and analyzed using methods that include matching collected data to published clinical guidelines and a decision-support tool algorithm to determine automatically which further clinical actions, e.g. actionable genetic tests, are indicated, and what personalized nutritional advice is likely to be acted upon.

According to an embodiment, the virtual agent and platform will use a custom-developed systematic and natural interview process to collect three- to four generation family medical histories, identify risks for the major familial disease syndromes, collect lifestyle data, such as twenty-four hour recall of nutritional intake data and make recommendations, e.g. actionable genetic testing based on both published guidelines and predictive modeling. It will also collect detailed dietary information on an ongoing basis to make dietary and lifestyle recommendations and provide critical data to researchers, e.g. nutrition researchers, pharmaceutical researchers, etc.

According to another embodiment, the platform expands to include a comprehensive health history focused on the full range of familial, lifestyle, and environmentally related diseases, enable data transfer to and from Electronic Medical Records (EMRs), facilitate ordering of genetic tests, and use predictive analytics to combine genotype and phenotype data to improve overall clinical recommendations. The VA with decision-support capabilities can identify new avenues of investigation to help physicians better identify patients who would benefit from precision-focused medical care than current practice allows.

In that respect, an EMR contains the standard medical and clinical data gathered in one provider's office. Conversely, Electronic health records (EHRs) go beyond the data collected in the provider's office and include a more comprehensive patient history. For example, EHRs are designed to contain and share information from all providers involved in a patient's care. EHR data can be created, managed, and consulted by authorized providers and staff from across more than one health care organization. Unlike EMRs, EHRs also allow a patient's health record to move with them—to other health care providers, specialists, hospitals, nursing homes, and even across states.

Aspect of the invention offers physicians, researchers, patients, health systems, and payers, a cost-effective and efficient, patient and provider friendly, evidence-based, means to continuously gather and analyze critical disease predisposition data. Consequently, embodiments of the invention accelerate the adoption of genetic testing of known clinical utility into routine medical practice, thereby aiding physicians in heralding a new era of precision medicine. Embodiments also allow "deep" phenotyping that is expected to increase genetic variant interpretation to improve medical diagnosis and treatment.

Embodiments of the invention provide a web-based tool that uses a Medi-tainment, conversational virtual assistant with decision support capabilities to continuously and cost-effectively and efficiently collect and analyze comprehensive structured patient data to make evidence-based recommendations for additional diagnostic evaluation(s), e.g. actionable genetic testing, so clinicians can provide more precise patient care. The VA enables collection of data using a convenient conversational-interview and Medi-tainment format, such that the patient does not have to review and/or understand various forms. Rather, the interview adapts to the user's level of health literacy and is directed to obtain the required responses and populate many of the forms using the responses, without the need for the user's interaction with the forms.

Disclosed embodiments provide a computerized method to solicit detailed health and personal data to develop a personalized phenotype classification, comprising: displaying an embodied virtual agent on a monitor; using the embodied virtual agent to engage in a conversational interview with a user, interspersed with a request for a response from the user; upon detection of each response from the user, performing the steps: determining whether the response is verbal and, if yes, applying the verbal response to a voice to text converter and converting the verbal response to text response, applying the text response to a natural language unit to generate a deciphered response; determining whether the deciphered response corresponds to detailed health or personal data and, if yes, storing the deciphered response in a user file; and, applying the deciphered response to a decision engine to determine an embodied virtual agent verbal dialog and an embodied virtual agent demeanor and applying the verbal dialog and demeanor to the embodied virtual agent. Disclosed embodiments also include computer readable media programmed to cause a computer to perform the steps of the computerized method.

Disclosed embodiments further provide a system for solicit detailed health and personal data to develop a personalized phenotype classification, comprising: an embodied virtual agent generator; a speech to text module; a natural language module; a structural input processor; a dialog manager/decision engine module; a natural language generator; a policy storage module; and a comprehensive health history database. The system may also include a decision support tool programmed to analyze the responses of the user and generate recommendations for genetic testing and/or nutritional counseling.

Other aspects and features of the invention would be apparent from the detailed description, which is made with reference to the following drawings. It should be mentioned that the detailed description and the drawings provide various non-limiting examples of various embodiments of the invention, which is defined by the appended claims.

BRIEF DESCRIPTION OF THE DRAWINGS

The accompanying drawings, which are incorporated in and constitute a part of this specification, exemplify the embodiments of the present invention and, together with the description, serve to explain and illustrate principles of the invention. The drawings are intended to illustrate major features of the exemplary embodiments in a diagrammatic manner. The drawings are not intended to depict every feature of actual embodiments nor relative dimensions of the depicted elements, and are not drawn to scale.

FIG. 5 illustrates a tabulating embodiment representing epigenetic, e.g. lifestyle or environmental exposure, related disease risks.

DETAILED DESCRIPTION

Figure 1:
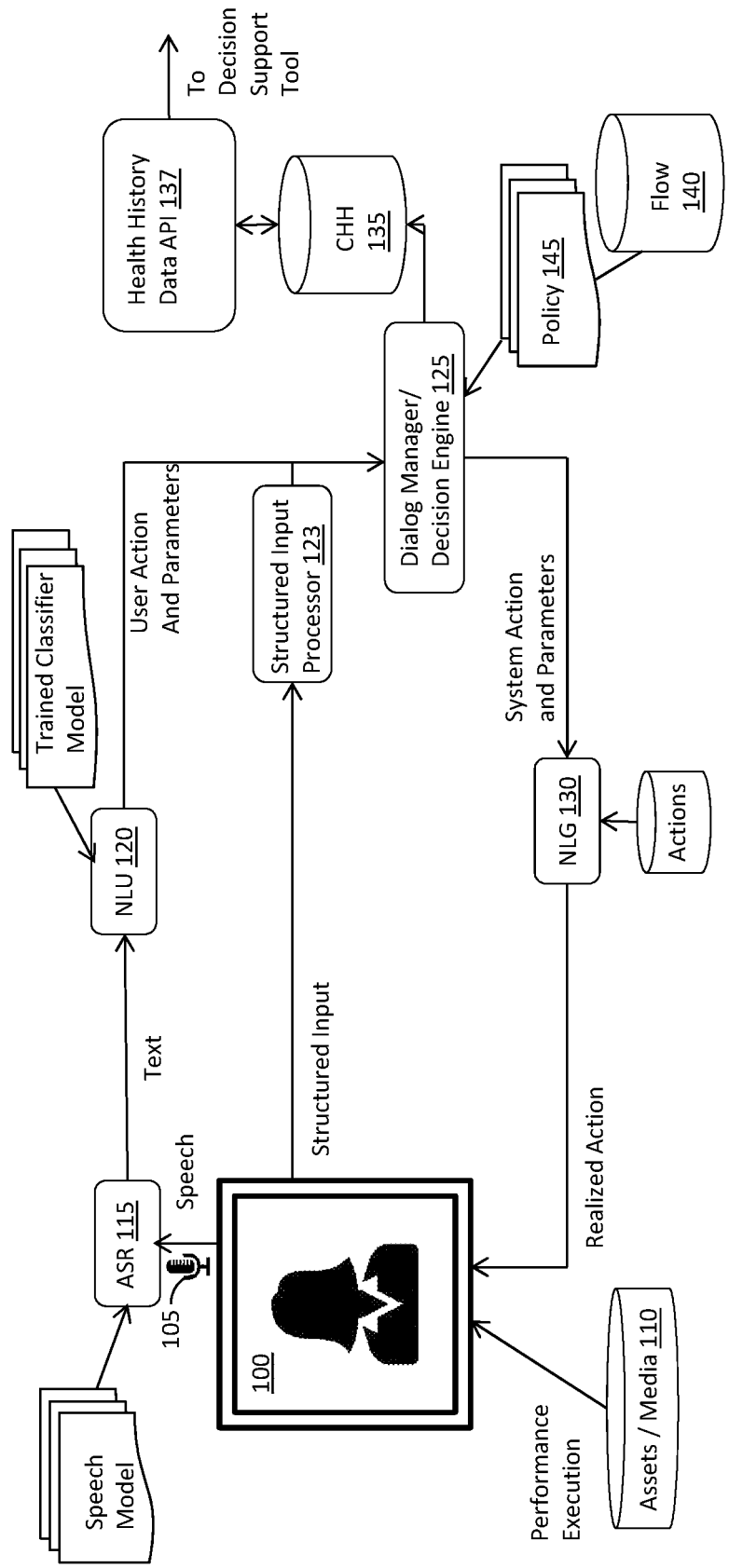
FIG. 1 is a block diagram illustrating the main components of the system according to one embodiment.

The following is a description of various embodiments and features highlighting some aspects of the invention. Various combinations of these features and aspects may be pursued in order to obtain the benefits of the disclosed invention.

Disclosed embodiments change the current paradigm in society for genetic counseling, and nutritional counseling, by providing a distributed virtual assistant that engages users in a Medi-tainment manner in a natural way to collect personal, medical, family, and environment history. The embodiments accomplish this change in paradigm by innovating in the following example key areas: using natural language to communicate with the user; recognizing user emotion and simulating appropriate emotion expression to build rapport with the user; using humor to build rapport and engagement, providing an automated recommendation about areas of medical concern and whether further testing, with appropriate specialists, is necessary; and using a new method to illustrate familial disease risk for medical use cases.

In the various disclosed embodiments, rather than engaging the patient in a face to face interview and/or requesting the patient to complete various electronic or paper forms to solicit various health information, a Virtual Assistant (VA) is used, that interacts and engages with the patient in a conversational/interview format, to solicit Comprehensive Health History (CHH). A Decision-Support Tool (DST), (the "GeneYes platform") addresses these challenges by: 1) utilizing an intelligent and conversational VA to engage the patient in the comfort of her own home and at her own pace so that a complete and accurate CHH can be obtained; 2) using motivational interviewing techniques that involve identifying the user's ambivalence by altering questions asked in response to not only the content of the users verbal inputs, but also in response to the user's word (mono versus polysyllabic) and sentence choices, tone, tenor, cadence, speed, and timing; 3) Medi-tainment, art of interspersing humor with clinical dialogue 4) assembling and storing the patient's response; 5) automatically analyzing this data, including correlating data to published guidelines, and offering decision-support to the primary care physician on par with recommendations a genetic counselor and/or nutritionist/dietician would provide given the same information; 5) providing a simple time- and cost-effective way for physicians to order indicated tests and electronically upload summary results and recommendations; 6) analyzing the results of available diagnostic testing in combination with the collected health data to adjust and explore additional avenues of investigation.

Embodiments of the GeneYes platform offer practitioners a new tool for predictive testing, risk stratification, and improved surveillance and treatment, and a new manner of visualizing such data for clinical decision support, thereby potentiating as great an advancement for medical practice as did blood chemistry testing. As early as the 19th century, many key blood chemistry disease marker tests were discovered. However, physicians' initial lack of training and comfort with these tests delayed for many years their adoption into routine medical practice. To avoid similar delays with genetic testing, a new approach is needed to accelerate adoption by practitioners.

The GeneYes platform offers a faster, inexpensive alternative with clear commercial potential as it will provide payers, providers and patients with validated decision-support information in a structured digital format immediately accessible to the medical record, needed to determine which patients will benefit from the increasing number of genetic tests with known clinical utility, as well as address nutritional and dietary needs. More precisely:

Payers cover genetic tests, but want to limit testing to appropriate indications. They need a tool that validates appropriate testing while nullifying unneeded testing for cost control. Payers will also value a tool that identifies opportunities for cost-effective clinical intervention that reduces overall costs. In addition, per the Affordable Care Act, 16 states now include some coverage and reimbursement for dietary or nutritional screening, counseling and/or therapy for obesity, sometimes including weight loss programs. An additional seven states cover nutritional counseling or therapy, but only for a diabetes-related diagnosis or treatment. In combination, some or all such coverage is required in 23 states. As a result, payers are looking for a cost-effective means to deliver nutritional counseling and therapy.

Providers want the best information for medical decision-making. However, most physicians have limited time to gather CHH and limited training in interpreting such data to choose appropriate genetic testing. A tool that collects and analyzes EMR uploadable structured-data both spares physicians from such efforts and reduces their need for ongoing additional training. Health systems that employ physicians financially benefit from identifying patients needing enhanced surveillance e.g. increased MRIs for cancer detection.

Patients prefer medical care that avoids or delays life-threatening diseases. They want reliable, actionable information. A direct-to-consumer lab, 23andMe, publicly reports that more than one million people have used its limited and non-clinician supervised genetic testing services. The FDA stopped 23andMe's offering of health risk assessments for two years, asserting that such testing requires proper supervision. 23andMe has now reinstated a more limited genetic testing service primarily directed at parents planning to have babies. The GeneYes platform complies with all relevant FDA regulations by including clinicians and focusing on the larger adult population with genetic predisposition(s) to major diseases.

Some embodiments of the GeneYes platform include a patient-facing web-based subscription service module where patients can ensure that their test results remain accurate and properly validated as advancements in genetic research emerge that reclassify previously known and unknown variants.

Genetic testing labs want more customers and will benefit from a stream of vetted patients as practitioners adopt the GeneYes platform. These labs may have electronic connectivity for access to such a network.

Data seekers (e.g., pharmaceutical companies) want quality anonymized phenotype-genotype data, and form a final potential market. 23andMe has reported multiple sales of its anonymized data to bio-pharma companies for tens of millions of dollars. GeneYes can also be a bio-pharma drug trial screening tool.

Most people don't know if they are at risk for familial disease or would benefit from genetic testing. Patients concerned about genetic disease predisposition must first find a knowledgeable doctor, of which there are relatively few or ask their primary care physician for referral to a genetic counselor/geneticist to get a lab order to undergo specific actionable testing. As time pressed doctors are currently not well trained or up-to-date on the need for such referrals, many patients may not be getting appropriate care. The GeneYes platform represents a cost-effective, patient and doctor friendly means to prescreen patients for appropriate testing and/or referral. By utilizing an intelligent and engaging VA integrated with a DST driven by a smart decision algorithm, this innovative platform gathers and analyzes patient data, and delivers findings and recommendations in a doctor and EHR-friendly format.

To overcome barriers for acquiring CHH data, The GeneYes platform incorporates an engaging and compelling assistive process utilizing a fully interactive VA incorporating Medi-tainment, made accessible through the web or as an app in a mobile device connected to service on the cloud. The VA is a fully autonomous and embodied agent that uses both verbal (e.g., speech) and non-verbal (e.g., gaze, gesturing) channels to provide a naturalistic experience much like a human face-to-face encounter. The conversational/interview and Medi-tainment format increases a patient's willingness to disclose health and mental health information. CHH collection is a detailed, lengthy task, perhaps one that is best completed over the course of several separate sessions.

Today, nutrition researchers gather nutritional intake data by calling research subjects on the phone and asking them what they ate the day before. This is an arduous and time-consuming process that involves calling the subjects over the phone at various times to ask the subject to recall what he or she ate during the previous day during the periods usually associated with breakfast, lunch, and dinner, as well as periods when one would be expected to consume snacks as between meals and at around bedtime. To properly capture this information, the researcher must ask detailed questions about the specifics of the food consumed and the quantity consumed. In order to do so, the researcher provides the research subject with a booklet of different graphical representations of container sizes. For example, if the research subject indicates she consumed cereal for breakfast. The researcher would ask in what container. If the research subject indicated the container was a bowl, the researcher would refer the subject to a specific page in the graphical booklet that would contain different size bowls drawn to various scales and ask her to choose the proper bowl. Then the researcher would ask the subject to turn to another page and ask her to choose how much the bowl was filled. It is difficult to have enough images to properly correspond to all size bowls and to all amounts in the bowl so the data is somewhat inaccurate. Then the researcher would ask the specific brand of cereal and the user would have to provide a brand name. All this information would have to be recalled from memory by the research subject and properly transmitted over the phone, sometimes more than 24 hours after the food was consumed. It is not always possible to reach the research subject over the phone.

Conversely, the web-based conversational virtual agent asks the same nutritional intake data questions but also collect the information in a novel manner. For example, when the research subject indicates she ate cereal, in one embodiment a bowl, a cup, and a hand would pop up on the screen. The subject would say either "bowl, "cup", or "hand". If she states "bowl," a standard bowl would appear and the bowl's size could be adjusted larger and smaller on the screen or by speaking "larger" or "smaller." In addition, the amount of material in the bowl corresponding to the cereal could also be adjusted larger or smaller by speaking or screen entry. Finally, a category of cereals would appear, e.g. cornflakes, wheat bran, etc. Then, after speaking the category, various brand names producing that type of cereal would appear. The research subject would then speak the brand name and all cereals under that brand would appear. The research subject would then speak the specific type of cereal for that brand. That would appear with a number and the user would speak the number. This would conclude collection of this data point. The process would repeat until the research subject reports that all foods and their quantities have been properly captured. Furthermore, this information will be summarized in an electronic format that can be exported and sent to the researcher. This process would be available 24 hours a day and the research subject could capture the data as she consumes the food, thereby improving recall and increasing the accuracy of the captured information.

In appearance, behavior and functional impact, the VA is capable of providing innovative clinical support solutions. The VA can engage users and serve their healthcare needs in an "always on" tireless, unbiased, standardized, and cost effective fashion. This capability provides new innovative options to enhance quality of care while saving real human resources for the higher level needs that are best served by a human provider.

Turning to FIG. 1, a block schematic of one embodiment is illustrated. The system can be implemented on one or more servers, or on the "cloud," and may include a client operating on a mobile device, e.g., iOS or Android device. In the embodiment of FIG. 1 the various modules are shown separate for better understanding, but some of these modules may be integrated with others. All of the modules are coupled to the rendering engine (not shown) that displays the VA on the monitor 100 (of a PC or mobile device) and provides the relevant audio output. The modules are also coupled to a microphone 105, to receive the patient's responses.

An assets/media module 110 generates the graphics and audio to render the VA and other graphics to be presented to the patient. The assets/media module controls the performance execution and media presentation. When the patient vocally responds to the VA, the microphone 105 picks up the audio, which is transmitted to the automatic speech recognition (ASR) module 115. The ASR module 115 converts the patient's spoken words to text. The text is then provided to the natural language understanding (NLU) module 120. The output of the NLU module 120 is then provided to the dialog manager/decision engine (DIVIDE) 125, which determines the actions to be taken in response to the patient's response. Also, when the patient responds using a structured input, e.g., selecting from a menu, filling a field of a form, etc., the structured input is processed by the structured input processor 123 and its output is provided to the DIVIDE 125. When the action to be taken involves a verbal response by the VA, the response is provided to the natural language generation (NLG) module 130 to convert the machine response into a natural language response. The NLG 130 generates an output indicating a realized action, e.g., having the VA speaks and/or presents on the screen forms or menu for the user's response.

The DIVIDE 125 may also generate data related to the patient's health, which is output to the comprehensive health history storage unit 135, which maintains a file of the patient. The CHH file is made available to the decision support tool (not shown) via the health history data API 137. Additionally, in determining the proper response, the DMDE module 125 interacts with a health information question flow module 140 and a policy module 145.

Figure 2:
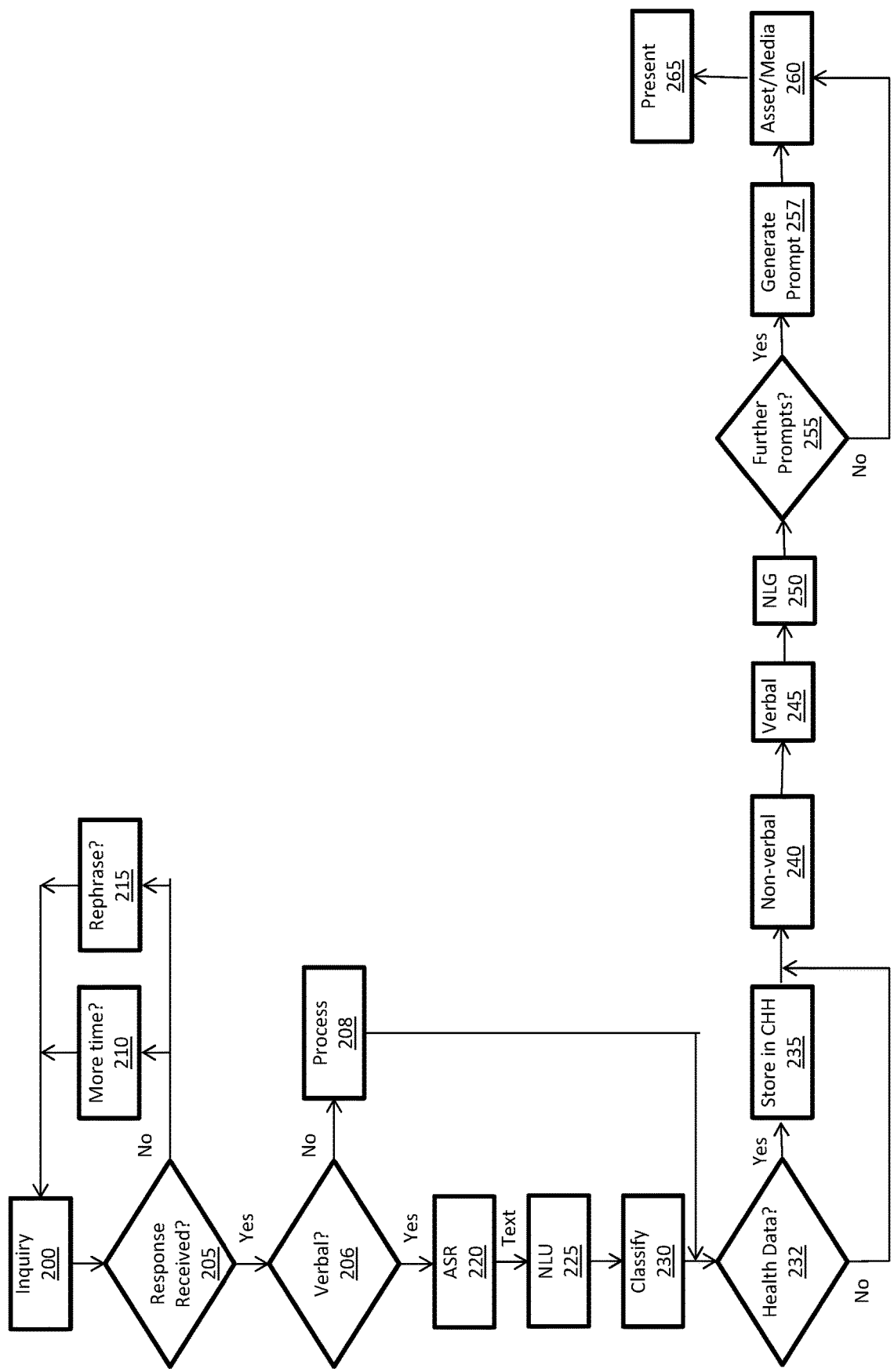
FIG. 2 is a flow chart illustrating a process according to one embodiment.

FIG. 2 is a flow chart illustrating a process according to one embodiment. The process may be executed by various combinations of the modules shown in FIG. 1, optionally in conjunction with a client running on a mobile device. In step 200 an inquiry is presented by the VA. The inquiry may be in the form of a question, a statement, a request for a response, etc., and may elicit a verbal or structural response from the user. The system then awaits the patient's response in step 205. If no response is received within an allotted time, the system may perform further prompting. For example, in step 210 it may ask the patient whether she needs more time or, in step 215 the system may rephrase the inquiry.

If in step 205 a response is received, in step 206 it is checked whether the response is verbal or structured. If the response is verbal (as opposed to structured, i.e., keyboard or mouse entry), in step 220 the response is operated upon by the automatic speech recognition (ASR) module to convert the verbal response into text. In step 225 the text is deciphered by the natural language understanding (NLU) module, in order to determine the meaning of the response. In step 230 the response, or various parts of the response, are classified. For example, parts may be determined to be health data to be added to the CHH, while other parts may be determined to require a response or follow up by the VA. In step 235 the parts that were classified as relating to the health of the patient, are stored as data in the CHH.

If in step 206 the response is non-verbal, it is provided to the structured input processor for processing in step 208. The output of the processor is then provided to the dialog manager/decision engine to process.

Then, in step 240 the system determines a non-verbal response to the patient's input. The non-verbal response may include, for example, demeanor of the VA, changes in the program flow, changes in the projected graphics, activation of a tutorial video, etc. In one embodiment the system stores, e.g., in a look-up table or otherwise, a number of facial expressions and a number of body gestures of the VA, so as to communicate attentiveness, enthusiasm, empathy, acknowledgement, and responsiveness. Depending on the response received from the user, the system selects a combination of facial expression and body expression, so as to enhance the verbal response of the VA.

In step 245 a verbal response is determined. The verbal response is provided to the natural language generator in step 250, in order to generate a natural language response to be used by the VA. In step 255 it is determined whether any further prompts need to be displayed graphically on the monitor. Such prompts may be, for example, a dialog box, display of written explanation or form, etc. Then in step 260 all the responses are applied to the performance execution/media presentation (assert media 110) in order to generate the proper response for the patient. The response is then rendered on the monitor 100 in step 265.

Figure 3A:
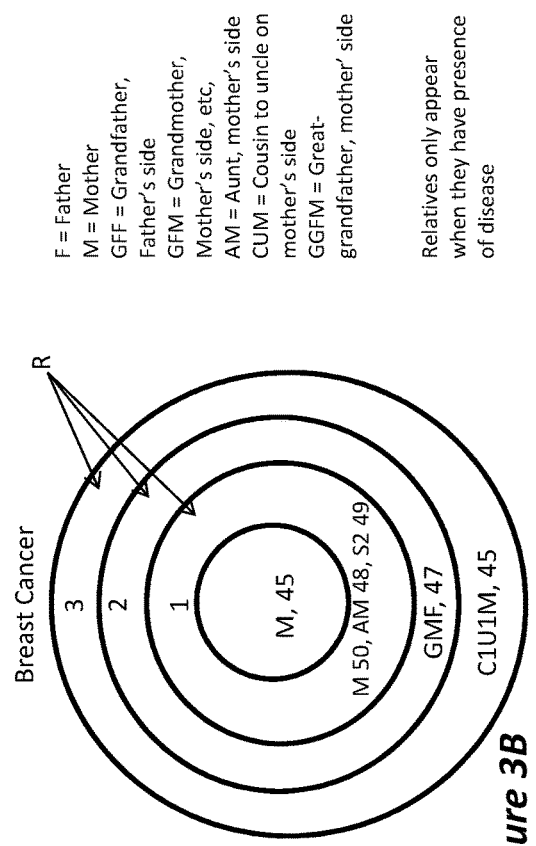
FIGS. 3A-3D demonstrate a new method of illustrating clinical familial and hereditary disease risk, which may be used in any of the disclosed embodiments.
Figure 3B:
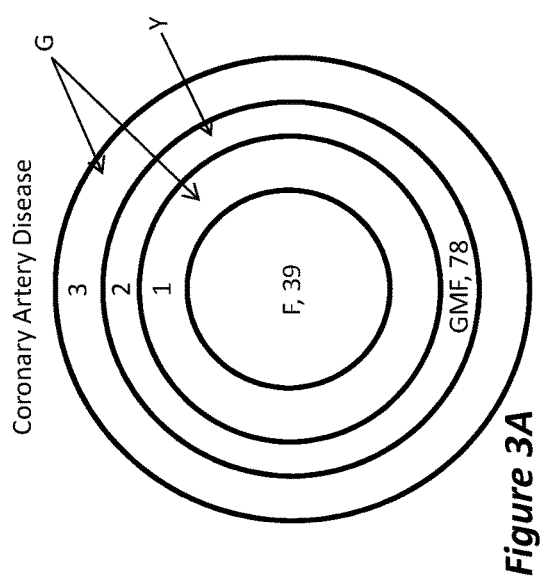
Figure 3D:
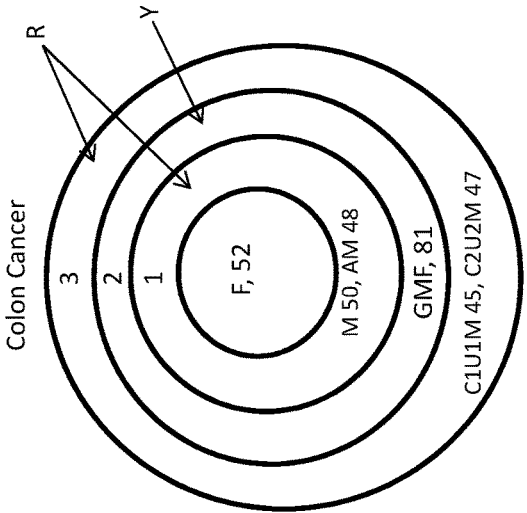
Figure 3C:
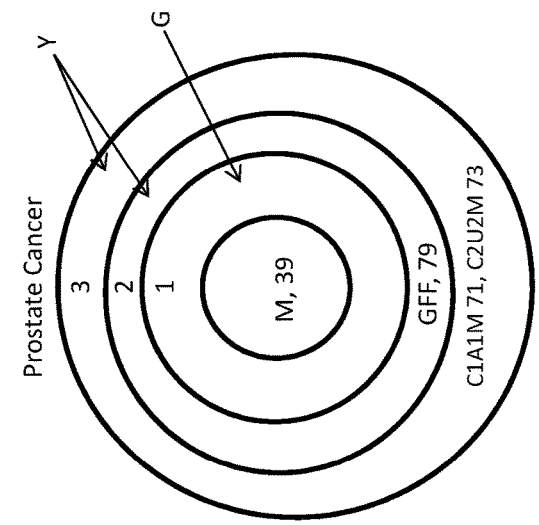

FIGS. 3A-3D demonstrate a new method of illustrating clinical familial and hereditary disease risk, which may be used in any of the disclosed embodiments. Each of FIGS. 3A-3D illustrates a schematic for one specific disease and a particular patient. As illustrated in FIGS. 3A-3D, each case is schematically presented using concentric circles. The center circle represents the patient (e.g., FIG. 3A is for a 39 years old female), and each concentric circle from the center represents the degree of relativity, i.e., the nearest concentric circle from the center (identified by numeral 1) represents first degree relatives that include parents, siblings, and children, the next outer concentric circle (identified by numeral 2) represents second-degree relatives that include an individual's grandparents, grandchildren, uncles, aunts, nephews, nieces, and half-siblings, and a third concentric circle farthest from the center (identified by numeral 3) represents third-degree relatives that include an individual's great-grandparents, great grandchildren, great uncles/aunts, and first cousins.

In the context of FIGS. 3A-3D, reference is made only to full or partial blood relatives, such as grandparents, parents, uncles, aunts, brothers and sisters, and children. Blood relatives are relatives that share DNA with the patient, which means they are related to the patient by birth, rather than by marriage, such as step kids, or adoption. By partial, it means that they are related by blood to at least one of the patient's parents or grandparents. For example, a half-brother would be someone who had the same mother, but a different father than the patient or the same father but different mother. And family that is related only by marriage, like a sister-in-law or uncle, who is married to the patient's father's sister, doesn't count in determining genetic or hereditary risk.

In addition, each circle is represented by one of three colors. To avoid using colors on patent application drawings, the colors are represented by Letter and arrow indicating which ring is colored by that color. Red (R) represents increased risk with family incidence of disease at a young age. Yellow (Y) represents moderate risk with family incidence of disease later in life, and green (G) represents an average level of risk with no family incidence of disease. Each circle represents any number of identifiable specific disease states such as breast cancer, prostate cancer and other cancers, cardiomyopathy and other heart diseases, hypercholesteremia, hemochromatosis, Alzheimer's, Parkinson's and other neurological diseases, etc. In some embodiments these circles will be displayed and illustrated in a dashboard format easily viewable for quick assessment of level of disease risk. Only disease states with high and moderate risk can be illustrated or all evaluated disease states. Colors for each circle are determined by the presence or absence of disease among generational relatives represented within that series of concentric circles. The color that encloses the name of the disease state illustrates the overall significance of family history in determining the need for further evaluation. In general, a green indicates no incidence of disease and would provide a recommendation to monitor. A yellow color indicates some family history and would recommend consideration of further evaluation. A red color indicates strong family history and definitively recommends further evaluation.

Embodiments of the invention aim to collect data to identify and potentially quantify risks, such as those discussed with respect to FIG. 3. However, the embodiments aim to collect such data without the use of a trained physician, but rather by use of the Medi-tainment trained VA. The questions asked and the responses from the patience may involve emotional reactions, which a trained physician may easily recognize and note. Similarly, the system needs to capture these reactions to enhance the understanding of the response. Therefore, in disclosed embodiments the virtual interviewer analyzes the voice and language patterns such as pitch, prosody (the patterns of stress and intonation in a language), speed, vocabulary content and complexity, etc. by creating data-driven representation of the interviewee speech sounds and text. The changes in the pitch, timing of the pauses between words, and sentences, the individual words and phrases are recorded and encoded as features into machine-based representation for each response. The specific representation may be a vector of numbers corresponding to individual features, a probability distribution over the occurrences of these features, or a stochastic process that captures how the features evolve over time. The interviewer system collects these representations and stores them in a database.

At the core of the interviewer is a parametric decision making function that uses the current state of the conversation database as input and produces the next question to ask as an output. This function has a number of parameters that condition the question selection process. The specific embodiment may utilize a Naive Bayes classifier, Support Vector Machine (SVM), a multilayered neural network, or any other parametric classifier.

This decision making function has to go through some initial machine learning process, where the system is presented with a number of desired interview interactions, the system attempts to replicate these interactions by analyzing the recorded answers and selecting the questions which content and order matches the sampled questions. The machine learning algorithm defines how the function parameters are adjusted to better mimic the sampled interviews. The specific learning algorithm will mostly depend on the data representation and decision function implementation. Some embodiments may include SVM, Reinforcement Learning, or Deep Learning.

Figure 4:
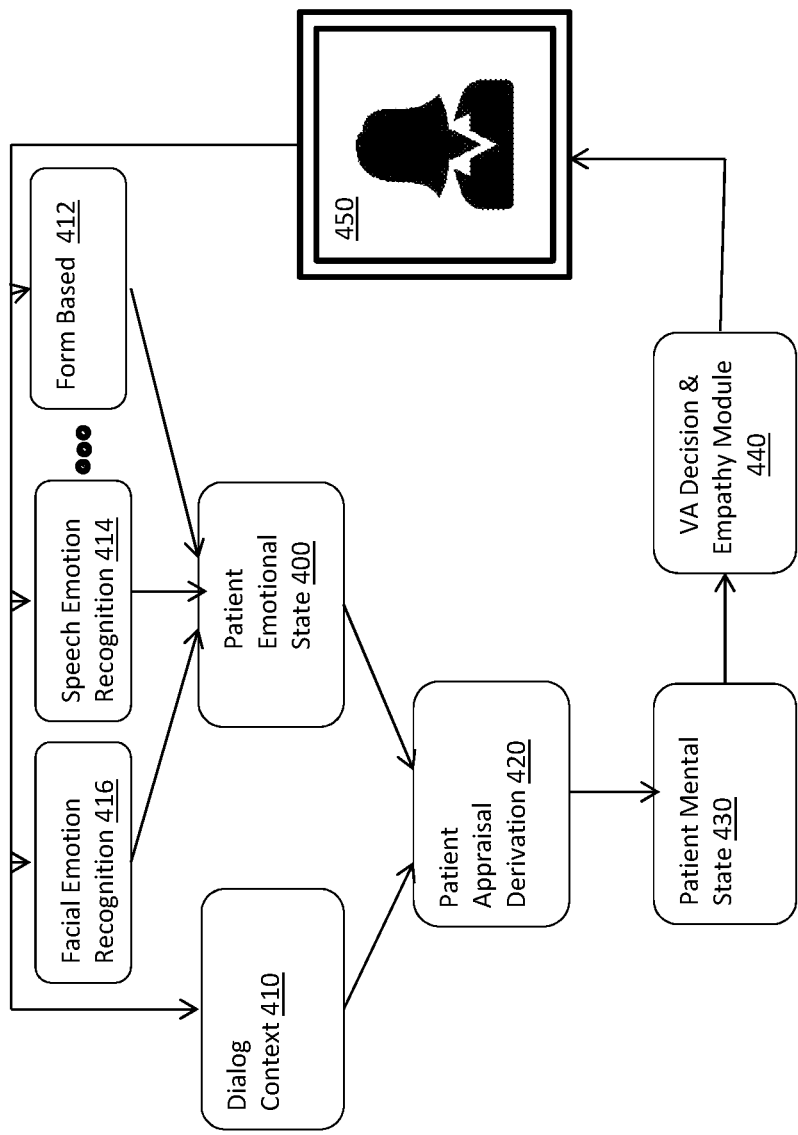
FIG. 4 is an illustration of and embodiment to simulate emotional expressions, via the virtual assistant, to build rapport and sustain engagement with the patient.

In order to enhance participation of the patient, disclosed embodiments simulate emotional expressions, via the virtual assistant, to build rapport and sustain engagement with the patient. One embodiment of this process is exemplified in FIG. 4. The user's response, including the live video stream of the patience is fed to individual emotion recognition modules. FIG. 4 illustrates three such modules, but more may be used, as indicated by the ellipsis. Each module employs techniques for recognizing emotion to determine the emotions the patient is experiencing at that time. The patient's current emotional state is stored in module 400. This state can be represented using a discrete set of labels ("happy", "sad", etc.) or continuous variables (e.g., "valence", "arousal", "dominance"). Using the stored patient emotional state stored in module 400, in conjunction with information about the current state of the dialogue stored in module 410, module 420 determine how is the patient appraising the ongoing interaction. These appraisal variables (module 430) capture the relevant aspects of the patient's mental state, including: Does the patient feel that providing information about his/her history is important for his/her goals? Does s/he feel it's worth making the effort to provide accurate and detailed information? Is the patient enjoying the interaction? Does the patient feel heard and respected by the virtual assistant? Is the patient tired? Is the patient distracted? Is the patient upset about something the virtual assistant did? Is the current topic sensitive to the patient? Etc.

Having inferred the patient's mental state, module 440 determines the virtual assistant's verbal and non-verbal response, as well as how the interaction should proceed. For instance, if the system determines that the patient is tired, the virtual assistant may react by encouraging the patient ("You are doing a great job!"), showing a smile, and proposing a short break. Once the virtual assistant reacts, a new cycle starts; thus, the system is continuously re-appraising the patient's mental state and responding accordingly.

As illustrated in FIG. 1, the collected data can be sent to a decision support tool that will translate established guidelines into a rule-based model for providing clinical decision support. Based on these recommendations, some users will undergo laboratory testing. The results of these tests will be used to continuously update the decision support tool using a machine learning method that will predict different risk-factors based on the collected clinical phenotypes. The new rules produced by the machine learning method will be reviewed by a panel of experts.

The machine learning method will also objectively rank the importance of all pieces of information collected. Over time, the ranking of importance will change as diseases develop or are avoided. This enables the exclusion of questions that provide little relevant information for clinical decision making and reduces the users' interaction time with the platform. Similarly, more in-depth phenotyping strategies will be designed for the areas considered by the method as high-value.

Based on the results of laboratory tests and continuously collected data, the machine learning method will identify areas in which further patient phenotyping should be prioritized (either to better understand the results of the laboratory test or to better characterize disease risk). This information will be used to automatically engage the user in a follow-up conversation to deepen their phenotypic information.

A second method of representing epigenetic, e.g. lifestyle or environmental exposure, related disease risks is described with reference to FIG. 5. The combination of certain epigenetic factors can markedly increase incidence of disease(s) that both patients and doctors need to anticipate for disease development and treatment. The juxtaposition of certain variants with certain lifestyle behaviors and/or environmental exposures can identify increased disease risk. Using a matrix format, one axis indicates identified pathogenic lifestyle behaviors and/or environmental exposures. As the line continues along the axis, the severity of the factor increases. A second axis indicates identified genetic variants known to be affected by lifestyle behaviors and/or environmental exposures. As the line extends along the axis the known pathogenicity in response to epigenetic factors of the variant increases. The matrix has nine quadrants identified as illustrated in FIG. 5.

Superimposed on quadrants where factors meet will be a third dimensional representation of risks associated with family medical history (not shown in FIG. 5). When there is an intersection of an epigenetic factor with a pathogenic variant, that quadrant is identified with a color that indicates the degree of attention warranted such as low/low, medium/low and low/medium are illustrated in green, medium/medium, high/low and low/high are illustrated in yellow and high/high, medium/high and high/medium are illustrated in red.

Today, most disease risk calculators simply provide a probability calculation for development of disease measured against normal population incidence. These calculators give a percentage, but don't explain or graphically illustrate what specifically caused the percentage increase and how different data points impacted the calculation. For example, knowing that you have twice the risk for developing breast cancer does not tell you what actions you or your physician should take and more importantly, when you should take them because of greatest risk. However, knowing that two first degree relatives died from the cancer before a certain age identifies both the specific age range you may be at increased risk and the need to identify what factors exist, such as genetic mutations that may explain the demonstrated incidence.

Figure 6:
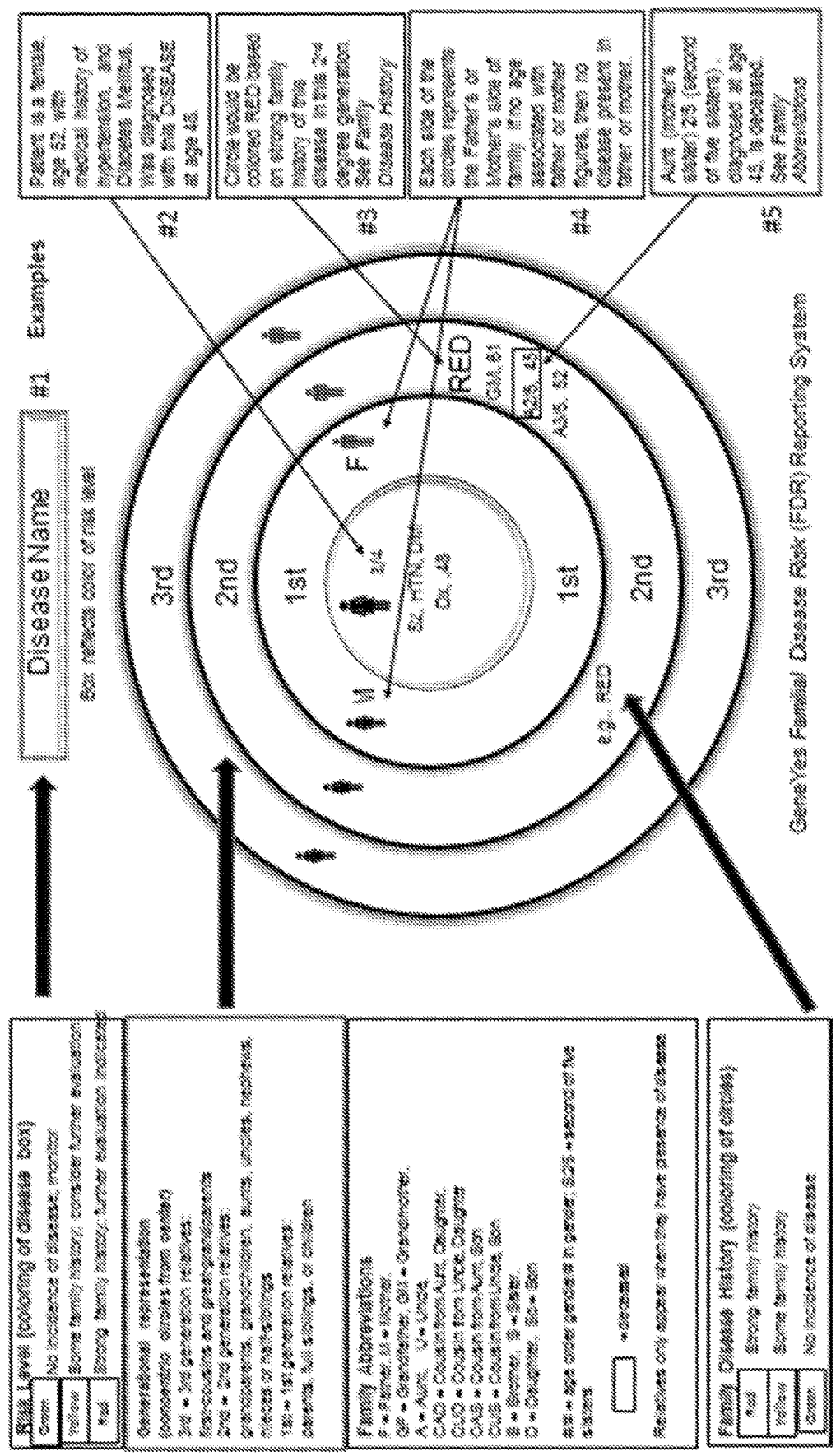
FIG. 6 illustrates another embodiment of the clinical familial and hereditary disease risk, which may be used in any of the disclosed embodiments.

As illustrated (see e.g., FIG. 6) and explained herein, we demonstrate a system that identifies generational risk while also providing specific data points of disease incidence, and most importantly, a quick graphical representation of overall disease predisposition across a spectrum of diseases, many for which no calculators currently exist. For the busy and harried physician, the combination of a data gathering tool, decision-support tool, and a new dashboard for graphical representation of data is expected to improve overall quality of care.

It should be understood that processes and techniques described herein are not inherently related to any particular apparatus and may be implemented by any suitable combination of components. Further, various types of general purpose devices may be used in accordance with the teachings described herein. It may also prove advantageous to construct specialized apparatus to perform the method steps described herein.

The present invention has been described in relation to particular examples, which are intended in all respects to be illustrative rather than restrictive. Those skilled in the art will appreciate that many different combinations of hardware, software, and firmware will be suitable for practicing the present invention. Moreover, other implementations of the invention will be apparent to those skilled in the art from consideration of the specification and practice of the invention disclosed herein. It is intended that the specification and examples be considered as exemplary only, with a true scope and spirit of the invention being indicated by the following claims.

The invention claimed is:

1. A computerized method to solicit detailed health and personal data from a user to develop and provide a personalized phenotype classification result that is reviewable by a physician, comprising:
   providing the user with a web application hosted on a digital platform stored in a computer-readable memory and executed by at least one server, the web application executable on an electronic device;
   displaying an embodied virtual agent capable of verbal and non-verbal communication, the virtual agent displayable on a visual display of the electronic device;
   using the embodied virtual agent to engage in a conversational interview with the user, including a request for an input response from the user, the request being displayable on the visual display of the electronic device,
   wherein the conversational interview is at least partially conducted using a parametric classifier that uses a database including data from a set of one or more previously conducted conversational interviews and one or more previous input responses from one or more users to select the request provided during the conversational interview,
   wherein the request prompts the user for the user's comprehensive family history, medical history, lifestyle history, nutritional history, or environmental exposure history;
   wherein the virtual agent is configured to simulate emotional expressions to engage the user; and
   wherein the virtual agent is configured to visually display images corresponding to a plurality of selectable options based on an input from the user relating to the user's nutritional history and to visually display another image based on a selection by the user of one of the first plurality of selectable options, a size of the another image being adjustable by the user to provide further input to the virtual agent relating to the user's nutritional history;
   the method further comprising, upon detection of a response to the request from the user, performing the steps:
      determining that the detected response is verbal, providing the detected response to a voice to text converter, converting the detected response to a text response, providing the text response to a natural language unit to generate a deciphered response, and determining a meaning of the deciphered response;
      determining that the deciphered response to the request includes at least a first portion that is medically related and, based thereon, determining that the deciphered response corresponds to the user's comprehensive family history, medical history, lifestyle history or environmental history and storing the deciphered response in a comprehensive health history file and
      determining that a second portion of the deciphered response is not medically related and, based thereon:
         (i) providing a follow up response to the user using the virtual agent; and
         (ii) not adding the second portion to the comprehensive health history file,
      wherein the comprehensive health history file includes a summary of family, medical, lifestyle and environmental exposure history; and
      providing a recommendation to the user to take at least one genetic test based on the deciphered response; and
      based on the deciphered response and a result of the at least one genetic test, automatically engaging the user in a follow-up conversation relating to phenotypic information associated with the user.

2. The method of claim 1, further comprising determining a verbal dialogue and demeanor for the embodied virtual agent to provide motivational interviewing techniques.

3. The method of claim 2, further comprising storing a plurality of embodied virtual agent facial expressions and a plurality of embodied virtual agent body gestures, and wherein determining the embodied virtual agent demeanor includes a selection from the plurality of facial expressions and a selection from the plurality of body gestures that demonstrate any one of empathy and interest.

4. The method of claim 2, further comprising the step of applying the embodied virtual agent verbal dialogue to a text to speech converter.

5. The method of claim 1, further comprising constructing a graphical illustration of clinical familial and hereditary disease risk.

6. The method of claim 5, wherein the graphical illustration comprises a graphical illustration of concentric circles having an innermost circle corresponding to the user, a first outer circle surrounding the innermost circle and a second outer circle surrounding the first outer circle, the first outermost circle corresponding to first full or partial relatives of the user, the second outer circle corresponding to second full or partial relatives of the user that are more removed from the user than the first full or partial relatives.

7. The method of claim 6, further comprising assigning colors to hereditary risk levels, and coloring the concentric circles according to the hereditary risk levels.

8. The method of claim 5, wherein the graphical illustration includes health factors.

9. The method of claim 8, wherein the health factors include the user's current medical history, risk factors for a specific disease, and genetic and familial factors.

10. The method of claim 9, wherein the genetic and familial factors are separated by generations.

11. The method of claim 1, wherein the recommended at least one genetic test is further determined based on predictive modeling.

12. A computerized method to solicit detailed health and personal data from a user to develop and provide a personalized phenotype classification result that is reviewable by a physician, comprising:
  providing the user with a web application hosted on a digital platform stored in a computer-readable memory and executed by at least one server, the web application executable on an electronic device;
  displaying an embodied virtual agent capable of verbal and non-verbal communication, the virtual agent displayable on a visual display of the electronic device;
  using the embodied virtual agent to engage in a conversational interview with the user, including a request for an input response from the user, the request being displayable on the visual display of the electronic device,
  wherein the request prompts the user for the user's comprehensive family history, medical history, lifestyle history, nutritional history, or environmental exposure history;
  the method further comprising, upon detection of a response to the request from the user, performing the steps:
    constructing a graphical illustration of clinical familial and hereditary disease risk, the graphical illustration including:
      a disease name corresponding to a disease; and
      a series of concentric circles having an innermost circle corresponding to the user, a first outer circle surrounding the innermost circle and a second outer circle surrounding the first outer circle, the first outer circle corresponding to first full or partial relatives of the user, the second outer circle corresponding to second full or partial relatives of the user that are more removed from the user than the first full or partial relatives,
    wherein the concentric circles are colored with different colors indicating different hereditary risk levels for the disease;
    wherein a graphical feature associated with the disease name is colored with a color indicating an overall significance of family history for the user with respect to the disease;
    wherein a first side of the series corresponds to the user's mother's family and a second side of the series opposite the first side corresponds to the user's father's family; and
    wherein for a circle indicating a first relative of the user who has had the disease, the circle includes indicia indicating a number of siblings of the first relative.

* * * * *